:

US011492328B2

United States Patent
Nickerl et al.

(10) Patent No.: US 11,492,328 B2
(45) Date of Patent: *Nov. 8, 2022

(54) BRANCHED URETHANE METHACRYLATE COMPOUNDS AND USE THEREOF

(71) Applicant: Hilti Aktiengesellschaft, Schaan (LI)

(72) Inventors: Georg Nickerl, Diessen am Ammersee (DE); Beate Gnass, Gersthofen (DE); Jens Bunzen, Augsburg (DE)

(73) Assignee: Hilti Aktiengesellschaft, Schaan (LI)

( * ) Notice: Subject to any disclaimer, the term of this patent is extended or adjusted under 35 U.S.C. 154(b) by 430 days.

This patent is subject to a terminal disclaimer.

(21) Appl. No.: 16/610,511

(22) PCT Filed: Jun. 25, 2018

(86) PCT No.: PCT/EP2018/066882
§ 371 (c)(1),
(2) Date: Nov. 3, 2019

(87) PCT Pub. No.: WO2019/007725
PCT Pub. Date: Jan. 10, 2019

(65) Prior Publication Data
US 2021/0155580 A1    May 27, 2021

(30) Foreign Application Priority Data

Jul. 3, 2017 (EP) ..................... 17179291

(51) Int. Cl.
| *C07C 271/28* | (2006.01) |
| *C08G 18/10* | (2006.01) |
| *C08G 18/24* | (2006.01) |
| *C08G 18/32* | (2006.01) |
| *C08G 18/67* | (2006.01) |
| *C08G 18/76* | (2006.01) |
| *C08K 3/34* | (2006.01) |
| *C08L 75/16* | (2006.01) |
| *C07C 219/32* | (2006.01) |

(52) U.S. Cl.
CPC .......... *C07C 271/28* (2013.01); *C07C 219/32* (2013.01); *C08G 18/10* (2013.01); *C08G 18/246* (2013.01); *C08G 18/3206* (2013.01); *C08G 18/672* (2013.01); *C08G 18/7671* (2013.01); *C08K 3/34* (2013.01); *C08L 75/16* (2013.01)

(58) Field of Classification Search
CPC ..... C07C 271/28; C07C 219/32; C08G 18/10; C08G 18/246; C08G 18/3206; C08G 18/672; C08G 18/7671; C08K 3/34; C08L 75/16
See application file for complete search history.

(56) References Cited

U.S. PATENT DOCUMENTS

| 4,281,078 | A | 7/1981 | Strolle et al. |
| 4,966,961 | A | 10/1990 | Tanabe et al. |
| 9,879,111 | B2 | 1/2018 | Leitner |
| 10,822,444 | B2 | 11/2020 | Messana et al. |
| 2001/0031838 | A1 | 10/2001 | Scott et al. |
| 2004/0072954 | A1 | 4/2004 | Udding et al. |
| 2015/0232595 | A1 | 8/2015 | Leitner et al. |
| 2015/0232610 | A1 | 8/2015 | Leitner |
| 2018/0319920 | A1 | 11/2018 | Messana et al. |

FOREIGN PATENT DOCUMENTS

| CA | 2280232 | 6/2000 |
| CN | 1038095 | 12/1989 |
| CN | 104311783 | 1/2015 |
| CN | 104755523 | 7/2015 |
| CN | 106009917 | 10/2016 |
| EP | 2 862 847 | 4/2015 |
| JP | 50-37701 | 12/1975 |
| JP | 53-28480 | 8/1978 |
| JP | 2004-516224 | 6/2004 |
| JP | 2015-532359 | 11/2015 |
| WO | 2014/064125 | 5/2014 |
| WO | 2017/066539 | 4/2017 |

OTHER PUBLICATIONS

Odian, G., Principles of Polymerization, Third Edition, John Wiley & Sons, Inc., 1991, pp. 29-33.*
He, et al., "*Research on the synthesis of UV curable tetra-functional acrylate resin with star-shaped structure*", Thermosetting Resin, vol. 23, No. 1, 2008, pp. 1-4, with English abstract.
International Search Report dated Sep. 13, 2018 in PCT/EP2018/066882 with English Translation.
Written Opinion dated Sep. 13, 2018 in PCT/EP2018/066882.

* cited by examiner

*Primary Examiner* — Patrick D Niland
(74) *Attorney, Agent, or Firm* — Grüneberg and Myers PLLC

(57) ABSTRACT

Branched urethane methacrylate compounds are useful as backbone resins for increasing the performance of a fastening material. Furthermore, reactive resins and reactive resin components containing such compounds are useful for chemical fastening.

16 Claims, No Drawings

BRANCHED URETHANE METHACRYLATE COMPOUNDS AND USE THEREOF

This application is a National Stage entry under § 371 of International Application No. PCT/EP2018/066882, filed on Jun. 25, 2018, and which claims the benefit of European Application No. 17179291,4, filed on Jul. 3, 2017.

BACKGROUND OF THE INVENTION

Field of the Invention

The invention relates to branched urethane methacrylate compounds as backbone resins, and to the use thereof in reactive resins, especially for increasing the performance capability of reactive resins containing such compounds and thus of reactive-resin components produced therefrom. Furthermore, the invention relates to the use of the reactive resins and of the reactive-resin components for construction purposes, especially for chemical fastening.

Discussion of the Background

The free-radical-curing fastening caulks currently in use are based on linear unsaturated polyesters, vinyl ester urethane resins and epoxy acrylates. These are mostly two-component reactive-resin systems, wherein one component is the resin (known as component (A)) and the other component (component (B)) contains the curing agent. Further ingredients such as inorganic fillers and additives, accelerators, stabilizers and reactive diluents may be contained in the one and/or the other component. By mixing the two components, the curing of the mixed components is initiated. During use of the fastening caulks for fastening of anchoring elements in drilled holes, the curing takes place in the drilled holes.

Such a fastening caulk is known, for example, from DE 3940138 A1. This describes fastening caulks on the basis of monomers that carry cycloaliphatic groups and may additionally contain unsaturated polyester or vinyl ester resins.

Disadvantages of these and of the resins commonly used heretofore in chemical fastening caulks are that they are substantially linear resins, which yield linear polymer chains. Hereby, however, the internal strength and thus the performance capability of a mortar is limited.

Therefore trifunctional or polyfunctional reactive diluents are frequently added to the fastening caulks, so that they may act as additional cross-linking agents, in order to achieve higher cross-linking between the polymer chains. This means, however, that the proportion of reactive diluents in the fastening caulks becomes higher, ultimately leading to reduction of the resin proportion in the caulk. Not uncommonly, the proportion of reactive diluents amounts to at least 50% relative to the reactive resin.

However, the use of high proportions of reactive diluents also leads to some disadvantages, which are manifested above all during use of the fastening caulk for fastening of anchoring means in drilled holes.

A considerable disadvantage is that the reduction of the proportion of highly viscous resin, which is essential for the performance capability of the caulk, negatively influences the performance capability of the cured fastening caulk.

A further disadvantage is greater shrinkage of the fastening caulk after curing, which may additionally influence the performance capability of the cured fastening caulk negatively. This is attributed to the fact that the contact between the cured fastening caulk and the undercuts, formed in the wall of the drilled hole during creation of the drilled hole, which become apparent in particular during use of percussion drills, is significantly reduced. This usually also prevents application of fastening caulks based on free-radical-curing compounds in diamond-drilled holes.

A further disadvantage is that, depending on type of reactive diluent, the proportion of volatile organic compounds (VOC) in the caulks may increase. This may lead to evaporation from the fastening caulk and/or the canister and possibly to a drop in performance of the cured fastening caulk that results from this. In addition, some of these compounds may also be hazardous to health and/or are therefore subject to mandatory labeling.

In addition, the number of usable reactive diluents is small, since only few available reactive diluents are on the market at present. Other than the free-radical-curing functional groups, the available reactive diluents have no or only a very limited choice of other functional groups and therefore often have only little influence on the property of the cured fastening caulk. This leads to the situation that the fastening caulks are being developed mostly for specific applications, such as certain temperature ranges, for example, or for application in specific substrates. This calls for an immense development effort in order to be able to address new and broader applications with the fastening caulks.

Heretofore special products have been produced, the formulations of which are adapted to the special application temperatures. Products indeed exist that are intended for a broad temperature range while still having the same properties over the entire range. Precisely in the boundary ranges, i.e. at low and at high temperatures, impairments must be expected either in processability, in curing of the caulk or in the properties of the cured caulk. No fastening caulk is known that covers a very broad temperature range without having to tolerate losses in the boundary ranges.

A need therefore exists for fastening caulks having performance capability and properties capable of being influenced not by the use of reactive diluents but instead by the resin ingredient.

SUMMARY OF THE INVENTION

One object of the present invention is to influence the properties of a reactive-resin master batch as well as of a reactive resin produced therefrom in a manner attributable solely to the structure of the backbone resin but not to the presence of additional compounds, such as reactive diluents or additives, for example. Mainly, the object of the present invention is to control the properties of a two-component or multi-component reactive-resin system by means of the backbone resin it contains.

Yet another object of the present invention is to provide a fastening caulk that avoids constituents posing a serious health hazard in the reactive-resin component and that optionally is also exempt from labeling. In particular, it is an object to reduce the proportion of reactive diluents in reactive resins for chemical fastening, without having to sacrifice their function or functions and positive effects on the cured fastening caulk.

Yet another object of the present invention is to provide a fastening caulk that is distinguished by good processability, curing behavior and small shrinkage over a broad temperature range and at the same time achieves higher load ratings of the cured fastening caulk than do conventional caulks.

These objects are solved by the compounds and the use thereof, by the reactive resin, and by the reactive-resin components according to various embodiments described below.

DETAILED DESCRIPTION OF THE INVENTION

Surprisingly, it has been found that, by the use of certain branched urethane methacrylate compounds as backbone resin, it was possible to increase the load ratings of a cured caulk.

For better understanding of the invention, the following explanations of the reactive-resin production method and of the terminology used herein are considered to be useful.

The reactive-resin production method, explained here by means of the example of an MDI-based urethane methacrylate, typically takes place as follows:

1. Production of Backbone-Resin/Reactive-Resin Master Batch

Methane diphenyl diisocyanate (MDI), hydroxypropyl methacrylate (HPMA) and trimethylol propane (TMP) are reacted in the presence of a catalyst and of an inhibitor (used to stabilize the backbone resin formed by the polymerization, and frequently also called stabilizer or process stabilizer). In this process, the backbone resin is obtained.

The reaction mixture obtained after the end of the reaction is known as reactive-resin master batch. This is not worked up further, i.e. the backbone resin is not isolated.

2. Production of Reactive Resin

After completion of the reaction to the backbone resin, an accelerator-inhibitor system, i.e. a combination of one or more additional inhibitors and one or more accelerators and optionally a reactive diluent, is added to the reactive-resin master batch.

Hereby the reactive resin is obtained.

The accelerator-inhibitor system is used to adjust the reactivity of the reactive resin, i.e. to adjust the point in time up to which the reactive resin has not yet cured completely after addition of an initiator and up to which point in time a plugging caulk mixed in with the reactive resin therefore remains processable after mixing with the initiator.

The inhibitor in the accelerator-inhibitor system may be identical to the inhibitor for the production of the backbone resin, provided this is also suitable for adjusting the reactivity, or it may be a different inhibitor if it does not possess both functions. As an example, 4-hydroxy-2,2,6,6-tetramethyl-piperidinyl-1-oxyl (TEMPOL) may be used as stabilizer and as inhibitor for adjustment of the reactivity.

3. Production of Reactive-Resin Component

In order to use the reactive resin for construction purposes, especially for chemical fastening, one or more inorganic aggregates, such as additives and/or fillers, are added after production of the reactive resin.

Hereby the reactive-resin component is obtained.

Within the meaning of the invention, the terms used:
"backbone resin" means a usually solid or highly viscous free-radical-curing polymerizable resin, which cures by polymerization (e.g. after addition of an initiator in the presence of an accelerator) and as a rule exists without reactive diluent and without further purification and thus may contain impurities;
"reactive master batch" means the reaction product of the reaction for production of the backbone resin, i.e. a mixture of backbone resin, reactive diluent and optionally further ingredients of the reaction mixture;
"reactive resin" means a mixture of reactive-resin master batch, at least one accelerator and at least one inhibitor (also referred to as accelerator-inhibitor system), at least one reactive diluent and optionally further additives; the reactive resin is typically liquid or viscous and may be further processed to a reactive-resin component; herein, the reactive resin is also referred to as "resin mixture";
"inhibitor" means a substance that suppresses an undesired free-radical polymerization during the synthesis or storage of a resin or of a resin-containing composition (these substances are also referred to in professional circles as "stabilizer") or that causes a time delay of free-radical polymerization of a resin after addition of an initiator (usually in conjunction with an accelerator) (these substances are also referred to in professional circles as "inhibitor"—the respective meaning of the term is apparent from the context);
"accelerator" means a reagent that participates with the initiator in a reaction, so that larger quantities of free radicals are already generated by the initiator at lower temperatures, or that catalyzes the decomposition reaction of the initiator;
"reactive diluent" means liquid or low-viscosity monomers and backbone resins, which dilute other backbone resins or the reactive-resin master batch and thereby impart the necessary viscosity for application thereof, which contain functional groups capable of reaction with the backbone resin and during polymerization (curing) become largely an ingredient of the cured caulk (e.g. of the mortar); reactive diluents are also called co-polymerizable monomers;
"reactive-resin component" means a liquid or viscous mixture of reactive resin and fillers as well as optionally further components, e.g. additives; typically, the reactive-resin component is one of the two components of a two-component reactive-resin system for chemical fastening;
"initiator" means a substance that forms reaction-initiating free radicals (usually in combination with an accelerator);
"hardener component" means a composition that contains an initiator for polymerization of a backbone resin; the hardener component may be solid or liquid and besides the initiator may contain a solvent as well as fillers and/or additives; typically, the hardener component in addition to the reactive-resin component is the other of the two components of a two-component reactive-resin system for chemical fastening;
"mortar caulk/fastening caulk" means the composition that is obtained by mixing the reactive-resin component with the hardener component and that may be used directly as such for chemical fastening;
"reactive-resin system" generally means a system that comprises components stored separately from one another, so that curing of the backbone resin contained in one component takes place only after mixing of the components;
"two-component system" or "two-component reactive-resin system" means a reactive-resin system that comprises two components stored separately from one another, a reactive-resin component (A) and a hardener component (B), so that curing of the backbone resin contained in the reactive-resin component takes place only after mixing of the two components;
"multi-component system" or "multi-component reactive-resin system" means a reactive-resin system that comprises several components stored separately from one another, including a reactive-resin component (A) and a hardener component (B), so that curing of the backbone resin contained in the reactive-resin component takes place only after mixing of all components;

"construction purposes" means any application for creation and maintenance or repair of building parts and building structures, as a polymer concrete, as a plastic-based coating caulk or as a cold-curing road marking; in particular, the reinforcement of building parts and building structures, for example walls, ceilings or floors, the fastening of building parts, such as panels or blocks, for example of stone, glass or plastic, on building parts or building structures, for example by adhesive bonding (constructional adhesive bonding) and quite particularly chemical fastening of anchoring means, such as anchor rods, bolts or the like in recesses, such as drilled holes;

"chemical fastening" means fastening (by substance-to-substance and/or interlocking joining) of anchoring means, such as anchor rods, bolts, rebars, screws or the like in recesses, such as drilled holes, especially in holes drilled in various substrates, especially mineral substrates, such as those on the basis of concrete, cellular concrete, brickwork, lime sandstone, sandstone, natural rock, glass and the like, and metallic substrates, such as those of steel;

"aromatic hydrocarbon group" means a cyclic, planar hydrocarbon group having an aromatic system, which on the basis of its delocalized electron system is energetically more favorable and therefore chemically more stable than its non-aromatic mesomers (PAC, 1995, 67, 1307; *Glossary of class names of organic compounds and reactivity intermediates based on structure* (IUPAC Recommendations 1995) page 1319);

"aromatic diisocyanate" means that the two isocyanate groups are bound directly to an aromatic hydrocarbon skeleton;

"(meth)acryl . . . / . . . (meth)acryl . . . " means that both the "methacryl . . . / . . . methacryl . . . " and the "acryl . . . / . . . acryl . . . " compounds are intended; preferably, "methacryl . . . / . . . methacryl . . . " compounds are intended in the present invention;

"a", "an", "any", as the indefinite article preceding a class of chemical compounds, e.g. preceding the word "urethane methacrylate", means that at least one, i.e. one or more compounds included under this class of chemical compounds, e.g. various urethane methacrylates, may be intended. In a preferred embodiment, only one individual compound is intended with this indefinite article;

"at least one" means numerically "one or more". In a preferred embodiment, "a", "an", "any" is meant numerically with this term;

"contain" and "comprise" mean that still further ingredients may be present in addition to those mentioned. These terms are intended to be inclusive and therefore also encompass "consist of". "Consist of is intended conclusively and means that no further ingredients may be present. In a preferred embodiment, the terms "contain" and "comprise" mean the term "consist of";

"approximately" or "circa" preceding a numerical value mean a range of ±5% of this value, preferably ±2% of this value, more preferably ±1% of this value, particularly preferably ±0% of this value (i.e. exactly this value);

a range limited by numbers means that the two extreme values and any value within this range are disclosed individually.

All standards cited in this text (e.g. DIN standards) were used in the version that was current on the date of filing of this Application.

A first subject matter of the invention is a compound of general formula (I)

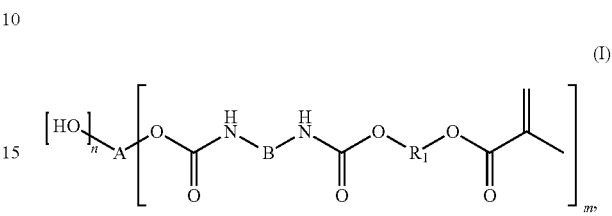

in which

B is an aromatic hydrocarbon group,

A is a linear or branched aliphatic $C_3$-$C_{10}$ alkylene group each $R_1$, respectively independently of one another, is a branched or linear aliphatic $C_1$-$C_{15}$ alkylene group n is a whole number greater than or equal to 0, and m is a whole number greater than or equal to 3.

A second subject matter is the use thereof for production of a reactive resin or a reactive-resin component for construction purposes. A third subject matter is the use thereof for increasing the bond strength of a cured fastening caulk. A fourth subject matter is a reactive resin comprising a compound of general formula (I), an inhibitor, an accelerator and optionally a reactive diluent. A fifth subject matter is a reactive-resin component for a reactive-resin system comprising the reactive resin. A sixth subject matter is a reactive-resin system, having the reactive-resin component and a hardener component, which contains an initiator. A seventh subject matter is the use of the reactive resin or of the reactive-resin system for construction purposes, especially for chemical fastening.

According to the invention, the branched urethane methacrylate compound is a compound of general formula (I)

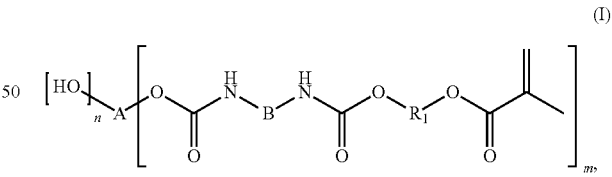

in which

B is an aromatic hydrocarbon group,

A is a linear or branched aliphatic $C_3$-$C_{10}$ alkylene group each $R_1$, respectively independently of one another, is a branched or linear aliphatic $C_1$-$C_{15}$ alkylene group n is a whole number greater than or equal to 0, and m is a whole number greater than or equal to 3.

In a preferred embodiment of the invention, the branched urethane methacrylate compound is a compound of general formula (II)

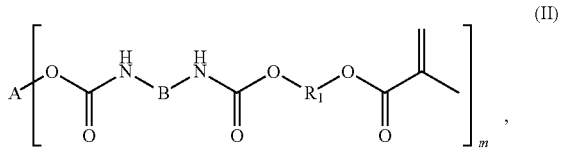

(II)

in which
B is an aromatic hydrocarbon group,
A is a linear or branched aliphatic $C_3$-$C_{10}$ alkylene group
each $R_1$, respectively independently of one another, is a branched or linear aliphatic
$C_1$-$C_{15}$ alkylene group, and
m is a whole number greater than or equal to 3.

The aromatic hydrocarbon group B is divalent and preferably has 6 to 20 carbon atoms and more preferably 6 to 14 carbon atoms. The aromatic hydrocarbon group may be substituted, especially by alkyl moieties, among which alkyl moieties having one to four carbon atoms are preferred.

In one embodiment, the aromatic hydrocarbon group contains a benzene ring, which may be substituted.

In an alternative embodiment, the aromatic hydrocarbon group contains two condensed benzene rings or two benzene rings bridged via an alkylene group, such as a methylene or ethylene group. Both the benzene rings and the alkylene bridges may be substituted, preferably with alkyl groups.

The aromatic hydrocarbon group is derived from aromatic diisocyanates, wherein "aromatic diisocyanate" means that the two isocyanate groups are bound directly to an aromatic hydrocarbon skeleton.

Suitable aromatic hydrocarbon groups are divalent groups, such as are obtained by removal of the isocyanate groups from an aromatic diisocyanate, for example a divalent phenylene group from a benzene diisocyanate, a methylphenylene group from a toluene diisocyanate (TDI) or an ethylphenylene group from an ethylbenzene diisocyanate, a divalent methane diphenylene group from a methane diphenyl diisocyanate (MDI) or a divalent naphthyl group from a naphthalene diisocyanate (NDI).

Particularly preferably, B is derived from 1,3-diisocyanatobenzene, 1,4-diisocyanatobenzene, 2,4-diisocyanatotoluene, 2,6-diisocyanatotoluene, 2,4'-diphenylmethane diisocyanate, 4,4'-diphenylmethane diisocyanate or 1,5-diisocyanatonaphthalene.

$R_1$, respectively independently of one another, is a branched or linear aliphatic $C_1$-$C_{15}$ alkylene group, which may be substituted. $R_1$ is derived from hydroxyalkyl methacrylates and comprises divalent alkylene groups, such as are obtained by removal of the hydroxyl groups and of the methacrylate ester group.

In one embodiment, the alkylene group $R_1$ is divalent.

In an alternative embodiment, however, it may also be trivalent or polyvalent, so that the compound of formula (I) may also have more than two methacrylate groups, even if this is not directly apparent from formula (I) or formula (II).

Preferably, the alkylene group $R_1$ is a divalent linear or branched $C_1$-$C_{15}$ alkylene group, preferably a $C_1$-$C_6$ alkylene group and particularly preferably a $C_1$-$C_4$ alkylene group. These include in particular the methylene, ethylene, propylene, i-propylene, n-butylene, 2-butylene, sec.-butylene, fort.-butylene, n-pentylene, 2-pentylene, 2-methylbutylene, 3-methylbutylene, 1,2-dimethylpropylene, 1,1-dimethylpropylene, 2,2-dimethylpropylene, 1-ethylpropylene, n-hexylene, 2-hexylene, 2-methylpentylene, 3-methylpentylene, 4-methylpentylene, 1,2-dimethylbutylene, 1,3-dimethylbutylene, 2,3-dimethylbutylene, 1,1-dimethylbutylene, 2,2-dimethylbutylene, 3,3-dimethylbutylene, 1,1,2-trimethylpropylene, 1,2,2-trimethylpropylene, 1-ethylbutylene, 2-ethylbutylene, 1-ethyl-2-methylpropylene, n-heptylene, 2-heptylene, 3-heptylene, 2-ethylpentylene, 1-propylbutylene groups or the octylene group, among which the ethylene, propylene and isopropylene groups more further preferred. In a particularly preferred embodiment of the present invention, the two $R_1$ groups are identical and are an ethylene, propyiene or i-propylene group.

The aliphatic $C_3$-$C_{10}$ alkylene group A acts as a skeleton, to which the urethane methacrylate groups are attached, and is a trivalent or polyvalent $C_1$-$C_{10}$ alkylene group, which is linear or branched.

Suitable linear or branched aliphatic $C_3$-$C_{10}$ alkylene groups are trivalent or polyvalent, preferably trivalent or tetravalent groups, as are obtained by removal of the hydroxyl groups from a tifunctional or polyfunctional alcohol, preferably trifunctional or tetrafunctional alcohol. Correspondingly suitable alcohols are, for example, glycerol, trimethylolmethane, trimethylolethane, trimethylolpropane, trimethylolbutane, 1,2,4-butanetriol, 1,2,3-hexanetriol, 1,2,4-hexanetiiol, pentaerythritol, diglycerol, triglycerol, bis(trimethylolpropane), sugars, such as, for example, glucose, sugar derivatives, such as, for example, sorbitol, mannitol, diglycerol, threitol, erythritol, adonitol (ribitol), arabitol (lyxitol), xylitol, dulcitol (galactitol), maltitol, isomaltitol, or polyesterol.

Hereby it is possible to obtain more than two free-radical-curing groups, namely the methacrylate groups, per compound, and so the compounds act as so-called cross-linking agents during the polymerization. By virtue of the further methacrylate group, the use of these compounds may lead to cross-linking between the formed polymer chains, so that a cross-linked polymer network can be formed.

Accordingly, m together with n (m+n) corresponds to the valence of the alcohol used for production of the inventive compound. Consequently, m=3 when a trifunctional alcohol is used and m+n=3 or 4 when a tetrafunctional alcohol is used.

By control of the reaction conditions, it is possible that not all hydroxyl groups react with an isocyanate group, and so free hydroxyl groups are still present in the resulting compound. These compounds are likewise comprised by the scope of the invention.

From this, compounds of general formula (I) result, in which n>0.

If all hydroxyl groups are converted, so that free hydroxyl groups are no longer present in the obtained compound, m alone (n=0) corresponds to the valence of the alcohol used for production of the inventive compound. Consequently, m=3 when a trifunctional alcohol is used and m=4 when a tetrafunctional alcohol is used.

From this, compounds of general formula (I) result, in which n=0, as shown in formula (II).

Preferably, n=0, 1 or 2 and m=3, 4 or 5, further preferably, n=0 or 1 and m=3 or 4 and particularly preferably, n=0 and m=3 or 4.

Preferably, n+m=3, 4, 5 or 6, particularly preferably, 3, 4 or 5, and quite particularly preferably, n+m=3 or 4, with the proviso that m≥3.

Preferably, n=0, 1 or 2 and m=2, 3 or 4 with n+m=3, 4, 5 or 6, more preferably, n=0 or 1 and m=2, 3 or 4 with n+m=3, 4 or 5, and particularly preferably, n=0 and m=3 or 4 (n+m=3 or 4), respectively with the proviso that m≥3.

The inventive urethane methacrylate compounds are obtained by reaction of a hydroxyalkyl methacrylate with a diisocyanate and an at least trifunctional alcohol. The hydroxyalkyl methacrylate, the diisocyanate and the alcohol are made to react in the presence of a catalyst and of an inhibitor, which acts to stabilize the resulting compound.

Suitable hydroxyalkyl methacrylates are such with alkylene groups having up to 15 carbon atoms, wherein the alkylene groups may be linear or branched. Hydroxyalkyl methacrylates having 1 to 10 carbon atoms are preferred. More preferred hydroxyalkyl methacrylates are such with two to six carbon atoms, among which 2-hydroxyethyl methacrylate, 2-hydroxypropyl methacrylate (2-HPMA), 3-hydroxypropyl methacrylate (3-HPMA) and glycerol 1,3-dimethacrylate are particularly preferred. 2-hydroxypropyl methacrylate (2-HPMA) or 3-hydroxypropyl methacrylate (3-HPMA) are quite particularly preferred.

Preferred aromatic diisocyanates are such with aromatically bound isocyanate groups, such as diisocyanatobenzene, toluene diisocyanates (TDI), diphenylmethane diisocyanates (MDI), diisocyanatonaphthalenes. These compounds may exist in different compositions both as pure compounds and as optical isomers or as isomer mixtures, which optionally may be separated in conventional manner.

Particularly preferred aromatic diisocyanates are 1,4-diisocyanatobenzene, 2,4-diisocyanatotoluene, 2,6-diisocyanatotoluene, 2,4'-diphenylmethane diisocyanate, 4,4'-diphenylmethane diisocyanate and 1,5-diisocyanatonaphthalene.

Suitable alcohols are trifunctional or multifunctional alcohols, selected from $C_3$-$C_{10}$ alcohols, preferable $C_3$-$C_4$ alcohols with the hydroxyl groups at the ends and/or along the alkyl chain. Examples of alcohols with at least three OH groups are glycerol, trimethylolmethane, trimethylolethane, trimethylolpropane, trimethylolbutane, 1,2,4-butanetriol, 1,2,3-hexanetriol, 1,2,4-hexanetriol, pentaerythritol, diglycerol, triglycerol, bis(trimethylolpropane), sugars, such as, for example, glucose, sugar derivatives, such as, for example, sorbitol, mannitol, diglycerol, threitol, erythritol, adonitol (ribitol), arabitol (lyxitol), xylitol, dulcitol (galactitol), maltitol, isomaltitol, or polyesterol, among which glycerol, trimethylolpropane and pentaerythritol are preferred.

Preferably, the inventive compounds of formula (I) are compounds of general formula (Ia), (Ib), (IIa) or (IIb):

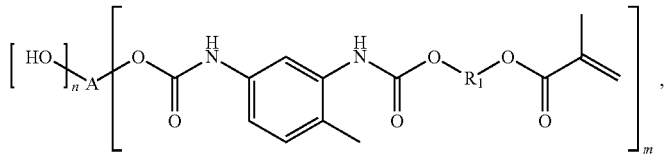

(Ia)

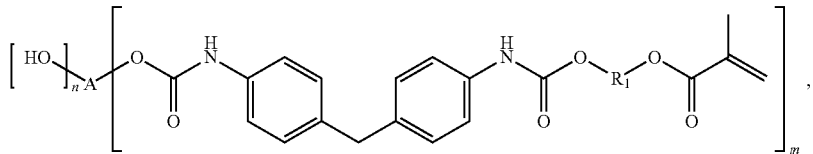

(Ib)

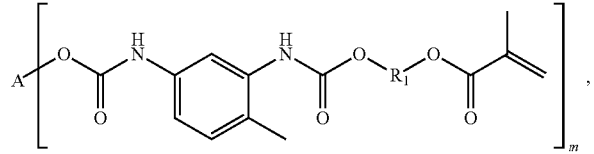

(IIa)

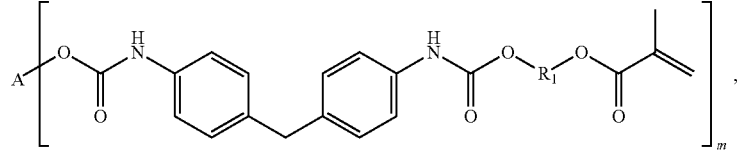

(IIb)

wherein respectively A, $R_1$, n and m are as defined hereinabove for formulas (I) and (II).

Particularly preferred inventive compounds are compounds of formulas (III) and (IV)

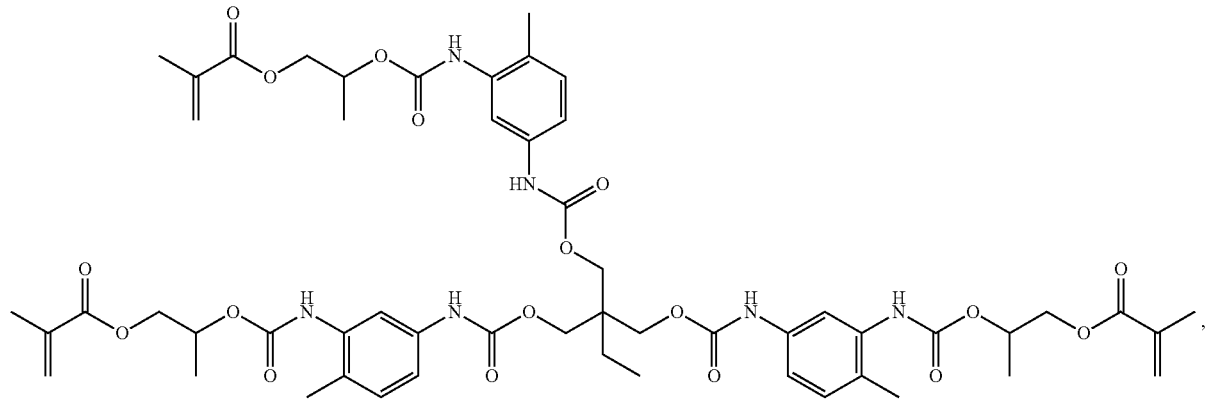

(III)

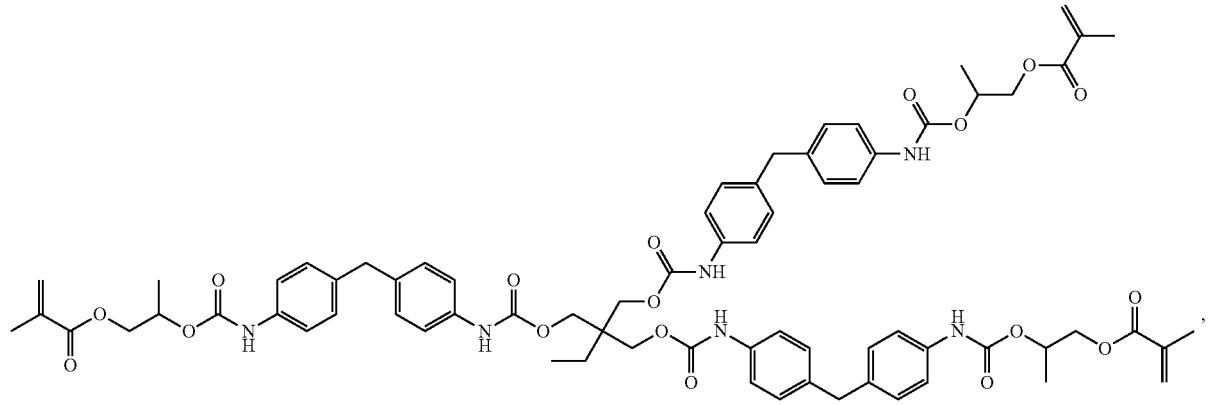

(IV)

The structures shown in formulas (I), (Ia), (Ib), (II), (IIa), (IIb), (III) and (IV) are intended to represent only examples of the inventive compounds, since the diisocyanates used for the production thereof may be used both as isomerically pure compounds and as mixtures of the different isomers, in respectively different compositions, i.e. in different quantitative ratios. The structures shown are therefore not to be construed as limitative.

Consequently, the inventive compounds exist as isomerically pure compounds or as isomer mixtures, in different compositions, which optionally may be separated in conventional manner. Both the pure isomers and the isomer mixtures are subject matter of the present invention. Mixtures containing different proportions of isomeric compounds are also subject matter of the invention.

Furthermore, depending on reaction control, especially by the ratio of isocyanate groups from the diisocyanate to hydroxyl groups from the hydroxymethyl acrylate, oligomers of the compounds of formulas (I) to (V) are formed, and so the compounds have an oligomer distribution. In each case, the oligomer together with a repeat unit is shown. However, the diagram showing a repeat unit is not to be construed as limitative, but instead is intended for clearer illustration. The oligomers that are not shown are comprised by the invention, to the extent that they are present.

For the case that not all isocyanate groups are converted during production of the inventive compounds, or that some of the isocyanate groups are opened prior to the reaction, for example by a side reaction, compounds are obtained which may be contained either as main compounds or as impurities in the reactive-resin master batch. To the extent that these compounds may be used for the inventive purposes, they are also comprised by the invention.

The compounds of formula (I) are used according to the invention for production of a reactive resin. Hereby cross-linking of the polymer chains and thus formation of a polymer network can be achieved. This may positively influence the performance capability of the cured caulk.

The inventive reactive resin contains a compound of formula (I) as described hereinabove as a backbone resin, an inhibitor, an accelerator and optionally a reactive diluent. Since the backbone resin, after its production, is typically used without isolation for production of the reactive resin, further ingredients, such as a catalyst, for example, contained in the reactive-resin master batch, are usually still also present in the reactive resin, besides the backbone resin.

The said inventive compounds may be used alone or in addition to other resins commonly used for the respective purpose of application of the reactive resin. In this way the cross-linking density of the polymer network may be influenced.

The proportion of the compound of general formula (I) in the inventive reactive resin ranges from 25 wt % to 65 wt %, preferably from 30 wt % to 45 wt %, particularly preferably from 35 wt % to 40 wt %, quite particularly preferably from 33 wt % to 40 wt % relative to the total weight of the reactive resin.

The stable free radicals that are commonly used for free-radical-curing polymerizable compounds, such as N-oxyl free radicals, as are known to the person skilled in the art, are suitable as inhibitors.

The inhibitor may function on the one hand to suppress undesired free-radical polymerization during synthesis of the backbone resin or during storage of the reactive resin and of the reactive-resin component. It may also function—optionally additionally—to cause a time delay of the free-radical polymerization of the backbone resin after addition of the initiator, and thereby to adjust the processing time of the reactive resin or of the reactive-resin component after mixing with the curing agent.

As examples of stable N-oxyl radicals, such may be used as described in DE 199 56 509 A1 and DE 195 31 649 A1. Such stable nitroxyl free radicals are of the piperidinyl-N-oxyl or tetrahydropyrrole-N-oxyl type or a mixture thereof.

Preferred stable nitroxyl free radicals are selected from the group consisting of 1-oxyl-2,2,6,6-tetramethylpiperidine, 1-oxyl-2,2,6,6-tetramethylpiperidine-4-ol (also known as TEMPOL), 1-oxyl-2,2,6,6-tetramethylpiperidine-4-one (also known as TEMPON), 1-oxyl-2,2,6,6-tetramethyl-4-carboxyl-piperidine (also known as 4-carboxy-TEMPO), 1-oxyl-2,2,5,5-tetramethylpyrrolidine, 1-oxyl-2,2,5,5-tetramethyl-3-carboxylpyrrolidine (also known as 3-carboxy-PROXYL) and mixtures of two or more of these compounds, wherein 1-oxyl-2,2,6,6-tetramethylpiperidine-4-ol (TEMPOL) is particularly preferred.

Besides the nitroxyl free radical of the piperidinyl-N-oxyl or tetrahydropyrrole-N-oxyl type, one or more further inhibitors may be present not only for further stabilization of the reactive resin or of the reactive-resin component (A) containing the reactive resin or of other compositions containing the reactive resin but also for adjustment of the resin reactivity.

The inhibitors that are commonly used for free-radical-curing polymerizable compounds, as are known to the person skilled in the art, are suitable for this purpose. Preferably, these further inhibitors are selected from among phenolic compounds and non-phenolic compounds and/or phenothiazines.

Phenols, such as 2-methoxyphenol, 4-methoxyphenol, 2,6-di-tert-butyl-4-methylphenol, 2,4-di-tert-butylphenol, 2,6-di-tert-butylphenol, 2,4,6-trimethylphenol, 2,4,6-tris(dimethylaminomethyl)phenol, 4,4'-thio-bis(3-methyl-6-tert-butylphenol), 4,4'-isopropylidenediphenol, 6,6'-di-tert-butyl-4,4'-bis(2,6-di-tert-butylphenol), 1,3,5-trimethyl-2,4,6-tris(3,5-di-tert-butyl-4-hydroxybenzyl)benzene, 2,2'-methylene-di-p-cresol, catechols, such as pyrocatechol, and catechol derivatives, such as butyl pyrocatechols, such as 4-tert-butyl pyrocatechol and 4,6-di-tert-butyl pyrocatechol, hydroquinones, such as hydroquinone, 2-methylhydroquinone, 2-tert-butylhydroquinone, 2,5-di-tert-butylhydroquinone, 2,6-di-tert-butylhydroquinone, 2,6-dimethylhydroquinone, 2,3,5-trimethylhydroquinone, benzoquinone, 2,3,5,6-tetrachloro-1,4-benzoquinone, methylbenzoquinone, 2,6-dimethylbenzoquinone, naphthoquinone, or mixtures of two or more thereof, are suitable as phenolic inhibitors. These inhibitors are often ingredients of commercial free-radical curing reactive-resin components.

Phenothiazines, such as phenothiazine and/or derivatives or combinations thereof, or stable organic free radicals, such as galvinoxyl and N-oxyl free radicals, for example, but not of piperidinyl-N-oxyl or tetrahydropyrrole-N-oxyl type, such as aluminum-N-nitrosophenylhydroxylamine, diethylhydroxylamine, oximes, such as acetaldoxime, acetone oxime, methyl ethyl ketoxime, salicyloxime, benzoxime, glyoximes, dimethylglyoxime, acetone-O-(benzyloxycarbonyl)oxime and the like, may be preferably regarded as non-phenolic inhibitors.

Furthermore, pyrimidinol or pyridinol compounds substituted in para position relative to the hydroxyl group may be used as inhibitors, as described in Patent Specification DE 10 2011 077 248 B1.

Preferably, the further inhibitors are selected from the group of catechols, catechol derivatives, phenothiazines, tert-butylcatechol, Tempol or a mixture of two or more thereof. Particularly preferably, the further inhibitors are selected from the group comprising catechols and phenothiazines. The further inhibitors used in the examples are quite particularly preferred, preferably approximately in the quantities specified in the examples.

Depending on the desired properties of the reactive resin, the further inhibitors may be used either alone or as a combination of two or more thereof.

The inhibitor or the inhibitor mixture is added in the proportions common in the art, preferably in a proportion of approximately 0.0005 to approximately 2 wt % (relative to the reactive resin ultimately produced therewith), more preferably of approximately 0.01 to approximately 1 wt % (relative to the reactive resin), even more preferably from approximately 0.05 to approximately 1 wt % (relative to the reactive resin), even much more preferably from approximately 0.2 to approximately 0.5 wt % (relative to the reactive resin).

The compounds of general formula (I), especially for use in reactive resins and reactive-resin components for chemical fastening and structural adhesive bonding, are generally cured by peroxides as curing agents. The peroxides are preferably initiated by an accelerator, so that polymerization takes place even at low application temperatures. The accelerator is already added to the reactive resin.

Suitable accelerators known to the person skilled in the art are, for example, amines, preferably tertiary amines and/or metal salts.

Suitable amines are selected from among the following compounds: dimethylamine, trimethylamine, ethylamine, diethylamine, triethylamine, n-propylamine, di-n-propylamine, tri-n-propylamine, isopropylamine, diisopropylamine, triisopropylamine, n-butylamine, isobutylamine, tert-butylamine, di-n-butylamine, diisobutylamine, triisobutylamine, pentylamine, isopentylamine, diisopentylamine, hexylamine, octylamine, dodecylamine, laurylamine, stearylamine, aminoethanol, diethanolamine, triethanolamine, aminohexanol, ethoxyaminoethane, dimethyl-(2-chloroethyl)amine, 2-ethylhexylamine, bis-(2-chloroethyl)amine, 2-ethylhexylamine, bis-(2-ethylhexyl)amine, N-methylstearylamine, dialkylamines, ethylenediamine, N,N'-dimethylethylenediamine, tetramethylethylenediamine, diethylenetriamine, permethyldiethylenetriamine, triethylenetetramine, tetraethylenepentamine, 1,2-diaminopropane, di-propylenetriamine, tripropylenetetramine, 1,4-diaminobutane, 1,6-diaminohexane, 4-amino-1-diethylaminopentane, 2,5-diamino-2,5-dimethylhexane, trimethylhexamethylenediamine, N,N-dimethylaminoethanol, 2-(2-diethylaminoethoxy)ethanol, bis-(2-hydroxyethyl)-oleylamine, tris42-(2-hydroxy-ethoxy)-ethyllamine, 3-amino-1-propanol, methyl-(3-aminopropyl) ether, ethyl-(3-aminopropyl) ether, 1,4-butanediol-bis(3-aminopropyl) ether, 3-dimethylamino-1-propanol, 1-amino-2-propanol, 1-diethylamino-2-propanol, diisopropanolamine, methyl-bis-(2-hydroxypropyl)amine, tris-(2-hydroxypropyl)amine, 4-amino-2-butanol, 2-amino-2-methylpropanol, 2-amino-2-methyl-propanediol, 2-amino-2-hydroxymethylpropanediol, 5-diethylamino-2-pentanone, 3-methylamino-propionic acid nitrile, 6-aminohexanoic acid, 11-aminoundecanoic acid, 6-aminohexanoic acid ethyl ester, 11-aminohexanoic acid isopropyl ester, cyclohexylamine, N-methylcyclohexylamine, N,N-dimethylcyclohexylamine, dicyclohexylamine, N-ethylcyclohexylamine, N-(2-hydroxyethyl)-cyclohexylamine, N,N-bis-(2-hydroxyethyl)-cy clohexylamine, N-(3-aminopropyl)-cy clohexylamine, aminomethylcy cl ° hexane, hexahydrotoluidine, hexahydrobenzylamine, aniline, N-methylaniline, N,N-dimethylaniline, N,N-diethylaniline, N,N-dipropylaniline, isobutylaniline, toluidine, diphenylamine, hydroxyethylaniline, bis-(hydroxyethyl)aniline, chloroaniline, aminophenols, aminobenzoic acids and their esters, benzylamine, dibenzylamine, tribenzylamine, methyldibenzylamine, a-phenylethylamine, xylidine, diisopropylaniline, dodecylaniline, aminonaphthalene, N-methylaminonaphthalene, N,N-dimethylaminonaphthalene, N,N-dibenzylnaphthalene, diaminocyclohexane, 4,4'-diamino-dicyclohexylmethane, diamino-dimethyl-dicyclohexylmethane, phenylenediamine, xylylenediamine, diaminobiphenyl, naphthalenediamines, toluidines, benzidines, 2,2-bis-(aminophenyl)-propane, aminoanisoles, amino-thiophenols, aminodiphenyl ether, aminocresols, morpholine, N-methylmorpholine, N-phenylmorpholine, hydroxyethylmorpholine, N-methylpyrrolidine, pyrrolidine, piperidine, hydroxyethylpiperidine, pyrroles, pyridines, quinolines, indoles, indolenines, carbazoles, pyrazoles, imidazoles, thiazoles, pyrimidines, quinoxalines, aminomorpholine, dimorpholinethane, [2,2,21]-diazabicyclooctane and N,N-dimethyl-p-toluidine.

According to the invention, di-iso-propanol-p-toluidine or N,N-bis(2-hydroxyethyl)-m-toluidine is used as accelerator.

Preferred amines are aniline derivatives and N,N-bisalkylarylamines, such as N,N-dimethylaniline, N,N-diethylaniline, N,N-dimethyl-p-toluidine, N,N-bis(hydroxyalkyl)

arylamines, N,N-bis(2-hydroxyethyl)anilines, N,N-bis(2-hydroxyethyl)toluidine, N,N-bis(2-hydroxypropyl)aniline, N,N-bis(2-hydroxypropyl)toluidine, N,N-bis(3-methacryloyl-2-hydroxypropyl)-p-toluidine, N,N-dibutoxyhydroxypropyl-p-toluidine and 4,4'-bis(dimethylamino)diphenylmethane. Di-iso-propanol-p-toluidine is particularly preferred.

Polymeric amines, such as those obtained by polycondensation of N,N-bis(hydroxyalkyl)aniline with dicarboxylic acids or by polyaddition of ethylene oxide or other epoxides and these amines, are likewise suitable as accelerators.

Suitable metal salts are, for example, cobalt octoate or cobalt naphthenoate as well as vanadium, potassium, calcium, copper, manganese or zirconium carboxylates. Further suitable metal salts are the tin catalysts described hereinabove.

If an accelerator is used, it is introduced in a proportion of 0.01 to 10 wt %, preferably 0.2 to 5 wt % relative to the reactive resin.

The reactive resin may also contain a reactive diluent, if this is necessary. For this purpose, an excess of hydroxyfunctionalized (meth)acrylate optionally used during production of the backbone resin may function as the reactive diluent. In addition, if the hydroxyfunctionalized (meth)acrylate is used in approximately equimolar proportions with the isocyanate group, or additionally, if an excess of hydroxyfunctionalized (meth)acrylate is used, further reactive diluents, which are structurally different from the hydroxyfunctionalized (meth)acrylate, may be added to the reaction mixture.

Suitable reactive diluents are low-viscosity, free-radical-co-polymerizable compounds, preferably compounds exempt from labeling, which are added if necessary in order to adapt the viscosity among other properties of the urethane methacrylate or of the precursors during the production thereof.

Suitable reactive diluents are described in the Applications EP 1 935 860 A1 and DE 195 31 649 A1. Preferably, the reactive resin (the resin mixture) contains, as reactive diluent, a (meth)acrylic acid ester, wherein aliphatic or aromatic $C_5$-$C_{15}$ (meth)acrylates are selected particularly preferably. Suitable examples include: 2-hydroxypropyl (meth)acrylate, 3-hydroxypropyl (meth)acrylate, 1,2-ethanediol di-(meth)acrylate, 1,3-propanediol dimethacrylate, 1,3-butanediol di(meth)acrylate, 1,4-butanediol di(meth)acrylate, trimethylolpropane tri(meth)acrylate, phenylethyl (meth)acrylate, tetrahydrofurfuryl (meth)acrylate, ethyl triglycol (meth)acrylate, N,N-dimethylaminoethyl (meth)acrylate, N,N-dimethylaminomethyl (meth)acrylate, N,N-diethylaminoethyl (meth)acrylate, acetoacetoxyethyl (meth)acrylate, isobornyl (meth)acrylate, 2-ethylhexyl (meth)acrylate, tert-butylcyclohexyl (meth)acrylate, benzyl (meth)acrylate, methyl (meth)acrylate, n-butyl (meth)acrylate, isobutyl (meth)acrylate, 3-timethoxysilylpropyl (meth)acrylate, Isodecyl (meth)acrylate, diethylene glycol di(meth)acrylate, triethylene glycol di(meth)acrylate, methoxypolyethylene glycol mono(meth)acrylate, trimethylcyclohexyl (meth)acrylate, 2-hydroxyethyl (meth)acrylate, dicyclopentenyloxyethyl (meth)acrylate and/or tricyclopentadienyl di(meth)acrylate, bisphenol A (meth)acrylate, novolac epoxy di(meth)acrylate, di-[(meth)acryloyl-maleoyl]-tricyclo-5.2.1.0.2.6-decane, 3-(meth)acryloyl-oxymethyl-tricylo-5.2.1.0.2.6-decane, 3-(meth)cyclo-pentadienyl (meth)acrlate and decalyl-2-(meth)acrlate; PEG di(meth)acrylate, such as PEG200 di(meth)acrylate, tetraethylene glycol di(meth)acrylate, solketal (meth)acrylate, cyclohexyl (meth)acrylate, phenoxyethyl di(meth)acrylate, 2-phenoxyethyl (meth)acrylate, hexanediol-1,6-di(meth)acrylate, 1,2-butanediol di(meth)acrylate, methoxyethyl(meth)acrylate, butyldiglycol (meth)acrylate, tert-butyl (meth)acrylate and norbornyl (meth)acrylate. Methacrylates are preferred over acrylates.

2- and 3-Hydroxypropyl methacrylate, 1,2-ethanediol dimethacrylate, 1,4-butanediol dimethacrylate, 1,3-butanediol dimethacrylate, glycerol dimethacrylate, trimethylolpropane trimethacrylate, acetoacetoxyethyl methacrylate, isobornyl methacrylate, bisphenol A dimethacrylate, ethoxylated bisphenol A methacrylates such as E2BADMA or E3BADMA, trimethylcyclohexyl methacrylate, 2-hydroxyethyl methacrylate, PEG200 dimethacrylate and norbornyl methacrylate are particularly preferred and a mixture of 2- and 3-hydroxypropyl methacrylate and 1,4-butanediol dimethacrylate or a mixture of these three methacrylates is quite particularly preferred.

The most preferred is a mixture of 2- and 3-hydroxypropyl methacrylate. In principle, other common free-radical-polymerizable compounds may also be used as reactive diluents, alone or in a mixture with the (meth)acrylic acid esters, e.g. methacrylic acid, styrene, a-methylstyrene, alkylated styrenes, such as tert-butylstyrene, divinylbenzene and vinyl as well as allyl compounds, wherein the representatives thereof that are exempt from labeling are preferred. Examples of such vinyl or allyl compounds are hydroxybutyl vinyl ether, ethylene glycol divinyl ether, 1,4-butanediol divinyl ether, trimethylolpropane divinyl ether, trimethylolpropane trivinyl ether, mono-, di-, tri-, tetra- and polyalkylene glycol vinyl ethers, mono-, di-, tri-, tetra- and polyalkylene glycol allyl ethers, adipic acid divinyl ester, trimethylolpropane diallyl ether and trimethylolpropane triallyl ether.

The reactive diluent or diluents is or are added in a proportion up to 65 wt %, preferably up to 60 wt %, further preferably up to 55 wt %, particularly preferably in proportions below 50 wt %, relative to the reactive resin.

An exemplary reactive resin comprises a compound of general formula (I)

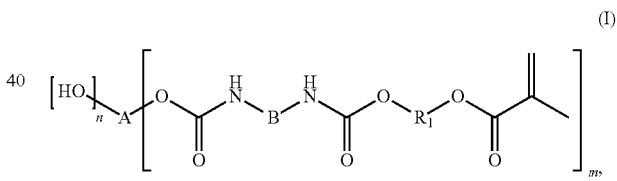

(I)

in which A, B, $R_1$, m and n are defined hereinabove, as the backbone resin, a stable nitroxyl radical as the inhibitor, a substituted toluidine as the accelerator and optionally a reactive diluent.

A preferred reactive resin comprises a compound of formula (II)

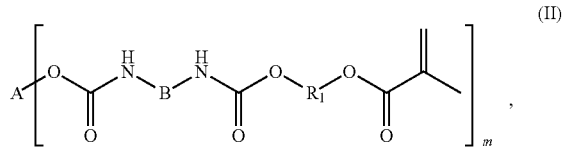

(II)

in which A, B, $R_1$ and m as are defined hereinabove, as the backbone resin, a stable nitroxyl radical as the inhibitor, a substituted toluidine as the accelerator and optionally a reactive diluent.

A further preferred reactive resin comprises a compound of formula (III) or (IV)

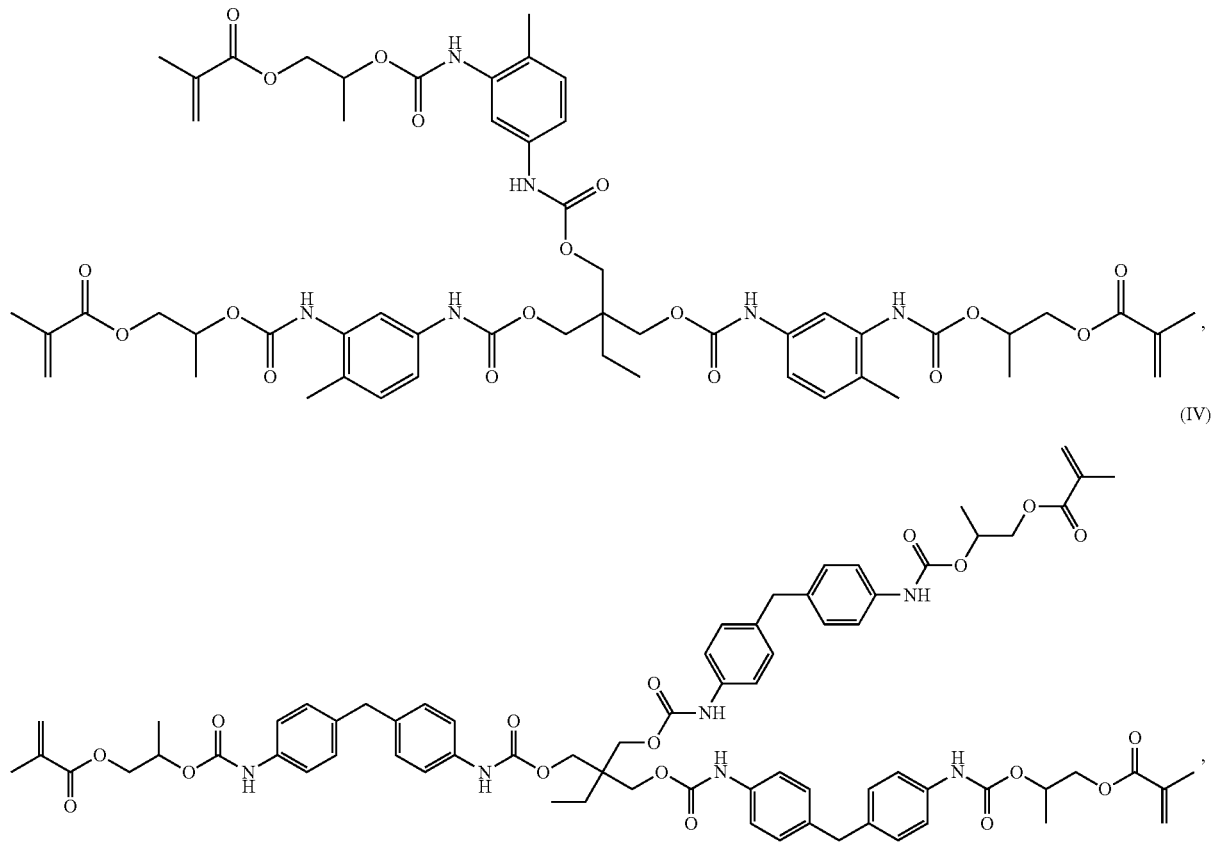

as the backbone resin, a stable nitroxyl radical as the inhibitor, a substituted toluidine as the accelerator and a reactive diluent.

A particularly preferred reactive resin comprises a compound of formula (II) or (IV) as the backbone resin, 4-hydroxy-2,2,6,6-tetramethyl-piperidinyl-1-oxyl (TEMPOL) as the inhibitor, di-iso-propanol-p-toluidine as the accelerator and a mixture of hydroxypropyl methacrylate and 1,4-butanediol dimethacrylate (BDDMA) as the reactive diluent.

By virtue of the branched backbone resin, an inventive reactive resin has the ability to form a polymer network, and so it is possible to produce, for a reactive-resin system, a reactive-resin component which, after curing thereof, exhibits an increased performance capability, especially increased load rating than do conventional systems, without the proportions of cross-linking reactive diluents needed heretofore for the purpose.

A further subject matter of the invention is a reactive-resin component that contains the reactive resin. The reactive-resin component may contain inorganic aggregates, such as fillers and/or additives, in addition to the inventive reactive resin. It should be pointed out that some substances, both as fillers and optionally in modified form, may also be used as additive. For example, fumed silica functions more as a filler in its polar, non-post-treated form and more as an additive in its apolar, post-treated form. In cases in which exactly the same substance can be used as filler or additive, the total quantity thereof should not exceed the upper limit stipulated herein for fillers.

For production of a reactive-resin component for construction purposes, especially chemical fastening, common fillers and/or additives may be added to the inventive reactive resin. These fillers are typically inorganic fillers and additives, such as described hereinafter by way of example.

The proportion of the reactive resin in the reactive-resin component preferably ranges from approximately 10 to approximately 70 wt %, more preferably from approximately 30 to approximately 50 wt %, relative to the reactive-resin component. Accordingly, the proportion of fillers preferably ranges from approximately 90 to approximately 30 wt %, more preferably from approximately 70 to approximately 50 wt %, relative to the reactive-resin component.

Common fillers, preferably mineral or mineral-like fillers, such as quartz, glass, sand, quartz sand, quartz flour, porcelain, corundum, ceramic, talc, silica (e.g. fumed silica, especially polar non-post-treated fumed silica), silicates, aluminum oxides (e.g. alumina), clay, titanium dioxide, chalk, heavy spar, feldspar, basalt, aluminum hydroxide, granite or sandstone, polymeric fillers such as thermosetting plastics, hydraulically curable fillers, such as gypsum, burnt lime or cement (e.g. aluminate cement (often also referred to as aluminous cement) or Portland cement), metals, such as aluminum, carbon black, further wood, mineral or organic fibers or the like, or mixtures of two or more thereof, are used as fillers. The fillers may exist in any desired forms, for example as powder or flour or as shaped bodies, e.g. in the form of cylinders, rings, balls, platelets, rods, shells or crystals, or further in fiber form (fibrillar fillers), and the corresponding basic particles preferably have a maximum diameter of approximately 10 mm and a minimum diameter of approximately 1 nm. This means that the diameter is approximately 10 mm or any value smaller than approximately 10 mm, but larger than approximately 1 nm. Preferably the maximum diameter is a diameter of approximately 5 mm, more preferably of approximately 3 mm, even more preferably of approximately 0.7 mm. A maximum diameter of approximately 0.5 mm is quite particularly preferred. The more preferred minimum diameter is approximately 10 nm, even more preferably approximately 50 nm, quite particularly preferably approximately 100 nm. Diameter ranges obtained by combination of this maximum diameter and minimum diameter are particularly preferred. However, the globular inert substances (spherical shape), which have a distinctly more reinforcing effect, are preferred. Core-shell particles, preferably with spherical shape, may also be used as fillers.

Preferred fillers are selected from the group consisting of cement, silica, quartz, quartz sand, quartz flour and mixtures of two or more thereof. Fillers selected from the group consisting of cement, fumed silica, especially untreated, polar fumed silica, quartz sand, quartz flour and mixtures of two or more thereof are particularly preferred for the reactive-resin component (A). A mixture of cement (especially aluminate cement (often also referred to as aluminous cement) or Portland cement), fumed silica and quartz sand is quite particularly preferred for the reactive-resin component (A). For the hardener component (B), fumed silica is preferred as the sole filler or as one of several fillers; particularly preferably, not only fumed silica but also one or more further fillers are present.

Common additives, i.e. thixotropic agents, such as, optionally, organically or inorganically post-treated fumed silica (except if it is already being used as filler), especially apolarly post-treated fumed silica, bentonites, alkyl and methyl celluloses, castor oil derivatives or the like, plasticizers, such as phthalic acid or sebacic acid ester, further stabilizers in addition to the stabilizers and inhibitors used according to the invention, antistatic agents, thickening agents, flexibilizers, rheology additives, wetting agents, coloring additives, such as dyes or especially pigments, for example for different coloration of the components to permit better control of intermixing thereof, or the like, or mixtures of two or more thereof, are used as additives. Non-reactive diluents (solvents) may also be included, preferably in a proportion of up to 30 wt % relative to the total quantity of the reactive-resin component, such as lower alkyl ketones, e.g. acetone, di-lower-alkyl lower alkanoylamides, such as dimethylacetamide, lower alkylbenzenes, such as xylenes or toluene, phthalic acid esters or paraffins, water or glycols. Furthermore, metal scavengers in the form of surface-modified fumed silicas may be contained in the reactive-resin component. Preferably, at least one thixotropic agent is present as additive, particularly preferably an organically or inorganically post-treated fumed silica, quite particularly preferably an apolarly post-treated fumed silica.

In this respect, reference is made to the Applications WO 02/079341 and WO 02/079293 as well as WO 2011/128061 A1.

The proportion of additives in the reactive-resin component may range up to approximately 5 wt %, relative to the reactive-resin component.

The reactive resins produced according to the invention can be used in many areas, in which unsaturated polyester resins, vinyl ester resins or vinyl ester urethane resins are otherwise commonly used. They are commonly used as resin ingredient in the reactive-resin component of a reactive-resin system, such as a multi-component system, typically a two-component system comprising a reactive-resin component (A) and a hardener component (B). This multi-component system can exist in the form of a cartridge system, a canister system or a film-bag system. During use of the system as intended, the components are extruded from the cartridges, canisters or film bags either by application or mechanical forces or by gas pressure, mixed with one another, preferably using a static mixer, through which the ingredients are conveyed, and applied.

Subject matter of the present invention is therefore also a reactive-resin system having a reactive-resin component (A) and a hardener component (B) as just described, that contains an initiator for the urethane methacrylate compound.

The initiator is customarily a peroxide. All peroxides known to the person skilled in the art that are used for curing of unsaturated polyester resins and vinyl ester resins may be employed. Such peroxides comprise organic and inorganic peroxides that are either liquid or solid, wherein hydrogen peroxide may also be used. Examples of suitable peroxides are peroxycarbonates (of the formula —OC(O)O—), peroxy esters (of the formula —C(O)OO—), diacyl peroxides (of the formula —C(O)OOC(O)—), dialkyl peroxides (of the formula —OO—) and the like. These may be present as oligomers or polymers.

Preferably, the peroxides are selected from the group of organic peroxides. Suitable organic peroxides are: tertiary alkyl hydroperoxides, such as tert-butyl hydroperoxide, and other hydroperoxides, such as cumene hydroperoxide, peroxy esters or peracids, such as tert-butyl peresters, benzoyl peroxide, peracetates and perbenzoates, lauryl peroxide, including (di)peroxy esters, perethers, such as peroxy diethyl ether, perketones, such as methyl ethyl ketone peroxide. The organic peroxides used as hardeners are often tertiary peresters or tertiary hydroperoxides, i.e. peroxide compounds with tertiary carbon atoms, which are bound directly to an —O—O-acyl- or —OOH— group. However, mixtures of these peroxides with other peroxides may also be used according to the invention. The peroxides may also be mixed peroxides, i.e. peroxides that have two different peroxide-carrying units in one molecule. Preferably, (dibenzoyl) peroxide (BPO) is used for curing.

The reactive-resin system may be present in the form of a two-component or multi-component system, in which the respective components exist spatially separated from one another, so that a reaction (curing) of the components take place only after they have been mixed.

A two-component reactive-resin system preferably comprises the A component and the B component separated, to ensure inhibition of reaction, into different containers, for example of a multi-chamber apparatus, such as a multi-chamber cartridge and/or canister, from which containers the two components are extruded by application of mechanical pressing forces or by application of a gas pressure and then mixed. A further possibility consists in packaging the two-component reactive-resin system as two-component capsules, which are introduced into the drilled hole and destroyed by percussively turning the fastening element to set it while simultaneously intermixing the two components of the mortar caulk. Preferably, a cartridge system or an injection system is used herein, in which the two components are extruded from the separated containers and passed through a static mixer, in which they are mixed homogeneously and then discharged via a nozzle, preferably directly into the drilled hole.

In a preferred embodiment of the inventive reactive-resin system, the reactive-resin system is a two-component system, and the reactive-resin component (A) contains not only the backbone resin but additionally also a hydraulically binding or polycondensable inorganic compound, especially cement, and the hardener component (B) contains not only the initiator for polymerization of the backbone resin but also water. Such hybrid mortar systems are described in detail in DE 4231161 A1. Therein, component (A) preferably contains cement as the hydraulically binding or polycondensable inorganic compound, for example Portland cement or aluminous cement, wherein cements free of transition metal oxides or low in transition metals are particularly preferred. Gypsum as such or mixed with the cement may also be used as the hydraulically binding inorganic compound. Component (A) may also comprise, as the polycondensable inorganic compound, silicatic polycondensable compounds, especially substances containing soluble, dissolved and/or amorphous silicon dioxide, such as, for example, polar, non-post-treated fumed silica.

The volume ratio of component A to component B in a two-component system is preferably 3:1, 5:1 or 7:1. A volume ratio of 3:1 or 5:1 is particularly preferred.

In a preferred embodiment, the reactive-resin component (A) therefore contains the following:
at least one urethane (meth)acrylate as defined hereinabove, preferably a compound of formula (IIa) or (IIb);
at least one inhibitor of piperidinyl-N-oxyl or tetrahydropyrrole-N-oxyl type as defined hereinabove, preferably TEMPOL;
at least one accelerator defined as hereinabove, preferably a toluidine derivative, particularly preferably di-iso-propanol-p-toluidine;
at least one hydraulically binding or polycondensable inorganic compound, preferably cement; and
at least one thixotropic agent, preferably fumed silica,
and the hardener component (B) contains:
at least one initiator for initiation of polymerization of the urethane (meth)acrylate, preferably benzoyl peroxide (BPO) or tert-butyl peroxybenzoate; and
water.

In a more preferred embodiment, the reactive-resin component (A) contains:
at least one urethane (meth)acrylate as defined hereinabove, preferably a compound of formula (IIa) or (IIb);
at least one inhibitor of piperidinyl-N-oxyl or tetrahydropyrrole-N-oxyl type as defined hereinabove, preferably TEMPOL;
at least one accelerator, preferably a toluidine derivative, particularly preferably di-iso-propanol-p-toluidine;
at least one hydraulically binding or polycondensable inorganic compound, preferably cement; and
at least one thixotropic agent, preferably fumed silica, and the hardener component (B) contains:
at least one initiator for initiation of polymerization of the urethane (meth)acrylate, preferably benzoyl peroxide (BPO) or tert-butyl peroxybenzoate;
at least one filler, preferably quartz sand or quartz flour; and
water.

In an even more preferred embodiment, the reactive-resin component (A) contains:
at least one urethane (meth)acrylate as defined hereinabove, preferably a compound of formula (IIa) or (IIb);
at least one inhibitor of piperidinyl-N-oxyl or tetrahydropyrrole-N-oxyl type as defined hereinabove, preferably TEMPOL;
at least one accelerator, preferably a toluidine derivative, particularly preferably di-iso-propanol-p-toluidine;
at least one further inhibitor, which is selected from the group consisting of catechols and phenothiazines;
at least one hydraulically binding or polycondensable inorganic compound, preferably cement; and
at least one thixotropic agent, preferably fumed silica, and the hardener component (B) contains:
at least one initiator for initiation of polymerization of the urethane (meth)acrylate, preferably benzoyl peroxide (BPO) or tert-butyl peroxybenzoate;
at least one filler, preferably quartz sand or quartz flour;
at least one thixotropic agent, preferably fumed silica; and
water.

In an even more preferred embodiment, the reactive-resin component (A) contains:
at least one urethane (meth)acrylate as defined hereinabove, preferably a compound of formula (III) or (IV);
at least one inhibitor of piperidinyl-N-oxyl or tetrahydropyrrole-N-oxyl type as defined hereinabove, preferably TEMPOL;
at least one accelerator, preferably a toluidine derivative, particularly preferably di-iso-propanol-p-toluidine;
at least one further inhibitor, which is selected from the group consisting of catechols and phenothiazines;
at least one hydraulically binding or polycondensable inorganic compound, preferably cement;
at least one thixotropic agent, preferably fumed silica; and
at least one further filler, preferably quartz sand,
and the hardener component (B) contains:
benzoyl peroxide (BPO) or tert-butyl peroxybenzoate as the initiator for initiation of polymerization of the urethane (meth)acrylate;
at least one filler, preferably quartz sand or quartz flour;
at least one thixotropic agent, preferably fumed silica; and
water.

In an even more preferred embodiment, the reactive-resin component (A) contains:
at least one urethane (meth)acrylate as defined hereinabove, preferably a compound of formula (III) or (IV);
TEMPOL;
di-iso-propanol-p-toluidine;
at least one further inhibitor, which is selected from the group consisting of catechols and phenothiazines;
cement;
fumed silica; and
quartz sand,
and the hardener component (B) contains:
at least one initiator for initiation of polymerization of the urethane (meth)acrylate;
fumed silica;
quartz sand or quartz flour and
water.

In each of these embodiments, the reactive-resin component (A) additionally contains, in a preferred embodiment, at least one reactive diluent.

In each of these embodiments, the reactive-resin components (A) and the hardener components (B) can be combined with one another in any desired manner.

Such a reactive-resin system is used above all in the building sector (construction purposes), for example for creation and maintenance or repair of building parts and building structures, for example of concrete, as a polymer concrete, as a plastic-based coating caulk or as a cold-curing road marking, for reinforcement of building parts and building structures, for example walls, ceilings or floors, the fastening of building parts, such as panels or blocks, for example of stone, glass or plastic, on building parts or building structures, for example by adhesive bonding (constructional adhesive bonding). It is particularly suitable for chemical fastening. It is quite particularly suitable for chemical fastening (by substance-to-substance and/or interlocking joining) of anchoring means, such as anchor rods, bolts, rebars, screws or the like in recesses, such as drilled holes, especially in holes drilled in various substrates, especially mineral substrates, such as those on the basis of concrete, cellular concrete, brickwork, lime sandstone, sandstone, natural rock, glass and the like, and metallic substrates, such as those of steel. In one embodiment, the substrate of the drilled hole is concrete and the anchoring means consists of steel or iron. In a further embodiment, the substrate of the drilled hole is steel and the anchoring means consists of steel or iron. For this purpose, the components are injected into the drilled hole, after which the devices to be fastened, such as threaded anchor rods and the like, are introduced into the drilled hole charged with the curing reactive resin and are appropriately adjusted.

The invention will be further explained on the basis of the following examples.

EXAMPLES

First of all, reactive-resin master batches, reactive resins, reactive-resin components and two-component reactive-resin systems respectively containing the inventive compound (III) or (IV) as backbone resin were produced. The bond strengths of the cured fastening caulks were determined.

A1.1 Production of Reactive-Resin Master Batch A1.1 with Compound (IV)

218 g Hydroxypropyl methacrylate and 669 g 1,4-butanediol dimethacrylate (BDDMA; Evonik AG) were first introduced into a 2-liter glass laboratory reactor with internal thermometer and stirrer shaft then 0.13 g phenothiazine (D Prills; Allessa Chemie), 0.37 g 4-hydroxy-2,2,6,6-tetramethyl-piperidinyl-1-oxyl (TEMPOL; Evonik Degussa GmbH), 0.23 g dioctyltin dilaurate (TIB KAT® 216; TIB Chemicals) and 67 g trimethylol propane (TMP) were added. The batch was heated to 100° C. Then 380 g diphenylmethane diisocyanate (MDI; TCI Deutschland GmbH) (3 equivalents per equivalent of TMP) was added dropwise with stirring (200 rpm) within 70 minutes. Thereafter stirring was continued for a further 300 minutes at 100° C. Finally, 666 g hydroxypropyl methacrylate was added.

Hereby reactive-resin master batch A.1 containing the compound (IV) as backbone resin was obtained. The product exists as an oligomer distribution, wherein the oligomer containing a repeat unit has the following structure:

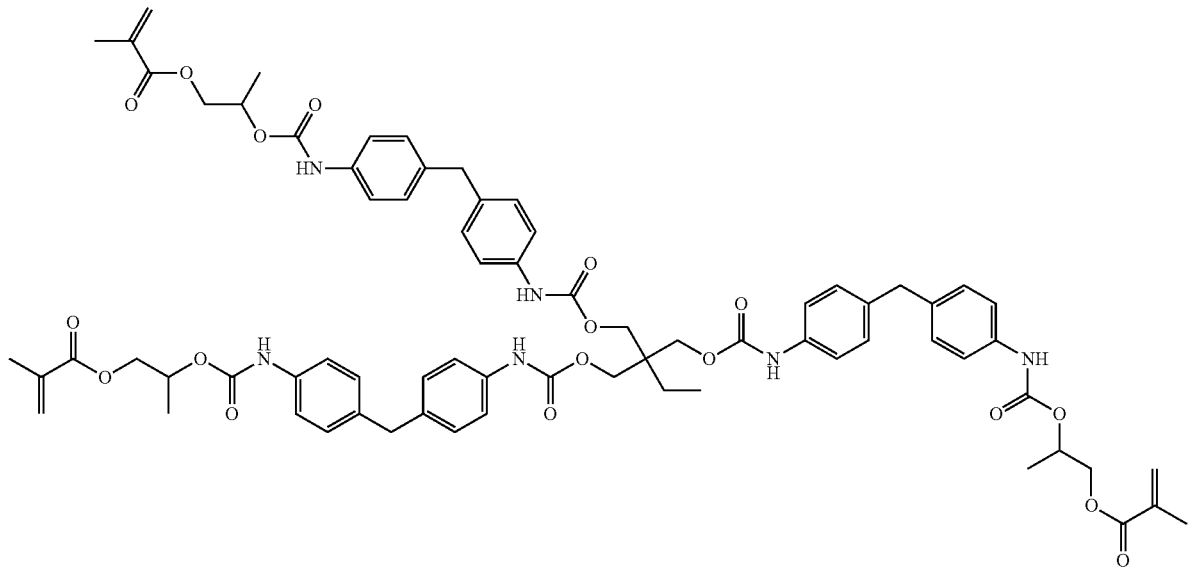

A1.2 Production of Reactive-Resin Master Batch A1.2 with Compound (IV)

300 g hydroxypropyl methacrylate and 660 g 1,4-butanediol dimethacrylate (BDDMA; Evonik AG) were first introduced into a 2-liter glass laboratory reactor with internal thermometer and stirrer shaft then 0.12 g phenothiazine (D Prills; Allessa Chemie), 0.29 g 4-hydroxy-2,2,6,6-tetramethyl-piperidinyl-1-oxyl (TEMPOL; Evonik Degussa GmbH), 0.21 g dioctyltin dilaurate (TIB KAT® 216; TIB Chemicals) and 31 g trimethylol propane were added. The batch was heated to 100° C. Then 348 g diphenylmethane diisocyanate MDI (6 equivalents per equivalent of TMP) was added dropwise with stirring (200 rpm) within 70 minutes. Thereafter stirring was continued for a further 300 minutes at 100° C. Finally, 660 g hydroxypropyl methacrylate was added.

Hereby reactive-resin master batch A.2 containing the compound (IV) as backbone resin was obtained. The product also exists as an oligomer distribution, but it is different from the product produced under A1.1.

A2.1 Production of Reactive Resin A2.1

6.0 g 4-Hydroxy-2,2,6,6-tetramethyl-piperidinyl-1-oxyl (TEMPOL; Evonik Degussa GmbH) and 22.8 g di-isopropanol-p-toluidine (BASF SE) were added to 1271 g reactive-resin master batch A1.1.

Hereby reactive-resin A2.1 containing the compound (IV) as backbone resin was obtained.

A2.2 Production of Reactive Resin A2.2

6.0 g 4-Hydroxy-2,2,6,6-tetramethyl-piperidinyl-1-oxyl (TEMPOL; Evonik Degussa GmbH) and 22.8 g di-isopropanol-p-toluidine (BASF SE) were added to 1271 g reactive-resin master batch A1.2.

Hereby reactive-resin A2.2 containing the compound (IV) as backbone resin was obtained.

The production of reactive resins A2.1 and A2.2 was carried out without addition of further reactive diluents.

A3.1 Production of Reactive-Resin Component A3.1

354 g Reactive resin A2.1 was mixed with 185 g Secar® 80 (Kerneos Inc.), 27 g Cab-O-Sil® TS-720 (Cabot Corporation) and 335 g quartz sand F32 (Quarzwerke GmbH) in the dissolver under vacuum, using a PC Labor System Dissolver of LDV 0.3-1 type. The mixture was stirred for 8 minutes at 3500 rpm under vacuum (pressure s 100 mbar) with a 55 mm dissolver disk and an edge scraper.

Hereby reactive-resin component A3.1 was obtained.

A3.2 Production of Reactive-Resin Component A3.2

354 g Reactive resin A2.2 was mixed with 185 g Secar® 80 (Kerneos Inc.), 27 g Cab-O-Sil® TS-720 (Cabot Corporation) and 335 g quartz sand F32 (Quarzwerke GmbH) in the dissolver under vacuum, by analogy with A3.1.

Hereby reactive-resin component A3.2 was obtained.

B1.1 Production of Reactive-Resin Master Batch B1.1 with Compound (III)

271 g Hydroxypropyl methacrylate and 657 g 1,4-butanediol dimethacrylate (BDDMA; Evonik AG) were first introduced into a 2-liter glass laboratory reactor with internal thermometer and stirrer shaft then 0.16 g phenothiazine (D Prills; Allessa Chemie), 0.39 g 4-hydroxy-2,2,6,6-tetramethyl-piperidinyl-1-oxyl (TEMPOL; Evonik Degussa GmbH), 0.28 g dioctyltin dilaurate (TIB KAT® 216; TIB Chemicals) and 83 g trimethylol propane were added. The batch was heated to 100° C. Then 328 g toluene diisocyanate (TDI; TCI Deutschland AG) (3 equivalents per equivalent of TMP) was added dropwise with stirring (200 rpm) within 45 minutes. Thereafter stirring was continued for a further 300 minutes at 100° C. Finally, 659 g hydroxypropyl methacrylate was added.

Hereby reactive-resin master batch B.1.1 containing the following compound (III) as backbone resin was obtained. The product exists as an oligomer distribution, wherein the oligomer containing a repeat unit has the following structure:

B1.2 Production of Reactive-Resin Master Batch B1.2 with Compound (III)

354 g Hydroxypropyl methacrylate and 660 g 1,4-butanediol dimethacrylate (BDDMA; Evonik AG) were first introduced into a 2-liter glass laboratory reactor with internal thermometer and stirrer shaft then 0.14 g phenothiazine (D Prills; Allessa Chemie), 0.34 g 4-hydroxy-2,2,6,6-tetramethyl-piperidinyl-1-oxyl (TEMPOL; Evonik Degussa GmbH), 0.24 g dioctyltin dilaurate (TIB KAT® 216; TIB Chemicals) and 37 g trimethylol propane were added. The batch was heated to 100° C. Then 286 g toluene diisocyanate (TDI; TC Deutschland AG) (6 equivalents per equivalent of TMP) was added dropwise with stirring (200 rpm) within 45 minutes. Thereafter stirring was continued for a further 300 minutes at 100° C. Finally, 662 g hydroxypropyl methacrylate was added.

Hereby the reactive-resin master batch B1.2 containing the compound (III) as backbone resin was obtained. The product also exists as an oligomer distribution, but it is different from the product produced under B1.1.

B2.1 Production of Reactive Resin B2.1

2.1 g 4-Hydroxy-2,2,6,6-tetramethyl-piperidinyl-1-oxyl (TEMPOL; Evonik Degussa GmbH) and 7.9 g di-iso-propanol-p-toluidine (BASF SE) were added to 440 g reactive-resin master batch B1.1.

Hereby reactive-resin B2.1 containing the compound (II) as backbone resin was obtained.

B2.2 Production of Reactive Resin B2.2

2.1 g 4-Hydroxy-2,2,6,6-tetramethyl-piperidinyl-1-oxyl (TEMPOL; Evonik Degussa GmbH) and 7.9 g di-iso-propanol-p-toluidine (BASF SE) were added to 440 g reactive-resin master batch B1.2.

Hereby reactive-resin B2.2 containing the compound (II) as backbone resin was obtained.

The production of reactive resins B2.1 and B2.2 was carried out without the addition of further reactive diluents.

B3.1 Production of Reactive-Resin Component B3.1

354 g Reactive resin B2.1 was mixed with 185 g Secar® 80 (Kerneos Inc.), 27 g Cab-O-Sil® TS-720 (Cabot Corporation) and 335 g quartz sand F32 (Quarzwerke) in the dissolver under vacuum, by analogy with A3.1.

Hereby reactive-resin component B3.1 was obtained.

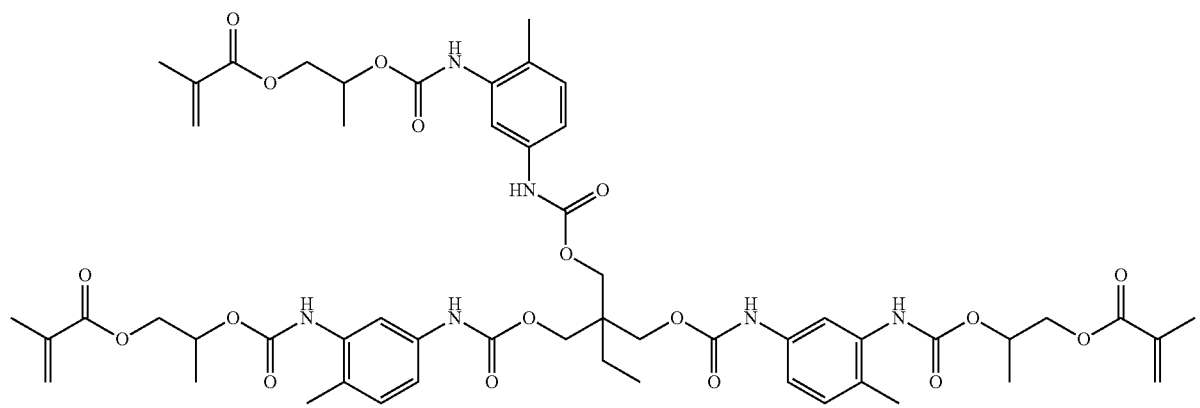 [SMILES: C=C(C)C(=O)OCC(C)OC(=O)Nc1cc(NC(=O)OCC(CC)(COC(=O)Nc2ccc(C)c(NC(=O)OC(C)COC(=O)C(=C)C)c2)COC(=O)Nc2ccc(C)c(NC(=O)OC(C)COC(=O)C(=C)C)c2)ccc1C]

3.2 Production of Reactive-Resin Component B3.2

354 g Reactive resin B2.2 was mixed with 185 g Secar® 80 (Kemeos Inc.), 27 g Cab-O-Sil® TS-720 (Cabot Corporation) and 335 g quartz sand F32 (Quarzwerke GmbH) in the dissolver under vacuum, by analogy with A3.1.

Hereby reactive-resin component B3.2 was obtained.

C1. Production of Comparison Reactive-Resin Master Batch C1 with Comparison Compound 1

The comparison reactive-resin master batch containing 65 wt % comparison compound 1 as backbone resin and 35 wt % hydroxypropyl methacrylate, relative to the total weight of the comparison reactive-resin master batch, was produced according to the method in EP 0 713 015 A1, which is included herewith as reference and to the entire disclosure of which reference is made.

The product (comparison compound 1) exists as an oligomer distribution, wherein the oligomer containing a repeat unit has the following structure:

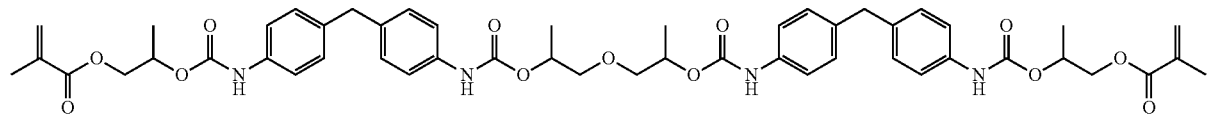

C2. Production of Comparison Reactive Resin C2

9.2 g 4-Hydroxy-2,2,6,6-tetramethyl-piperidinyl-1-oxyl (TEMPOL; Evonik Degussa GmbH) and 35.0 g di-isopropanol-p-toluidine (BASF SE) were added to a mixture of 1004 g comparison reactive-resin master batch C1, 300 g hydroxypropyl methacrylate and 652 g 1,4-butanediol dimethacrylate (BDDMA; Evonik AG).

Hereby comparison reactive-resin C2 containing the comparison compound 1 as backbone resin was obtained.

C3. Production of Comparison Reactive-Resin Component C3

354 g Comparison reactive resin C2 was mixed with 185 g Secar® 80 (Kemeos Inc.), 27 g Cab-O-Sil® TS-720 (Cabot Corporation) and 335 g quartz sand F32 (Quarzwerke GmbH) in the dissolver under vacuum, by analogy with A3.1.

Production of the Two-Component Reactive-Resin Systems

For production of the two-component reactive-resin systems A4.1, A4.2, B4.1 and B4.2 and of the comparison two-component reactive-resin system C4, the reactive-resin components A3.1, A3.2, B3.1 and B3.2 and respectively the comparison reactive-resin component C3 (component (A)) and in each case the hardener component (component (B)) of the commercially available product HIT HY-110 (Hilti Aktiengesellschaft; batch number: 1610264) were filled into plastic canisters (Ritter GmbH; volume ratio A:B=3:1) with inside diameters of 32.5 mm (component (A)) and respectively 14 mm (component (B)).

Hereby the two-component reactive-resin systems A4.1, A4.2, B4.1 and B4.2 as well as the comparison reactive-resin system C4 were obtained.

In order to demonstrate the influence of the inventive compounds (II) and (IV) on the bond strengths of a hardened fastening caulk, the bond strengths of the cured fastening caulks containing the reactive-resin components A3.1, A3.2, B3.1 and B3.2 were measured and compared with the bond strength of the cured fastening caulk containing the comparison reactive-resin components.

To measure the bond strengths (load ratings) of the cured fastening caulks, M12 threaded anchor rods were inserted into drilled holes in C20/25 concrete, which had a diameter of 14 mm and a drilled-hole depth of 72 mm and were filled with the fastening caulks. These drilled holes were cleaned, dust-free, dry and hammer-drilled; curing took place at 20° C. The temperature of the two-component reactive-resin system or of the fastening caulk during setting was 20° C. The bond strengths were determined by pulling out the threaded anchor bars centrally. Respectively five threaded anchor bars were set and the bond strength was determined after 24 hours of curing. The fastening caulks were extruded from the canisters and injected into the drilled holes via a static mixer (HIT-RE-M Mixer; Hilti Aktiengesellschaft).

The bond strengths ($N/mm^2$) determined in this way are listed as the mean value of five measurements in the following Table 1.

TABLE 1

Results of measurement of the bond strength of the cured fastening caulks containing the reactive-resin components A3.1, A3.2, B3.1 and B3.2 as well as of the cured fastening caulk containing the comparison reactive-resin component C3

|  | Bond strength [$N/mm^2$] |
|---|---|
| Fastening caulk with reactive-resin component A3.1 | 21.3 |
| Fastening caulk with reactive-resin component A3.2 | 19.4 |
| Fastening caulk with reactive-resin component B3.1 | 20.0 |
| Fastening caulk with reactive-resin component B3.2 | 18.2 |
| Comparison fastening caulk with comparison reactive-resin component C3 | 18.0 |

The results show that the fastening caulks produced with the inventive branched urethane methacrylate compounds, compound (II) and compound (IV), have higher bond strengths (load ratings) than the comparison fastening caulk produced with comparison compound 1.

The invention claimed is:

1. A compound, of the formula

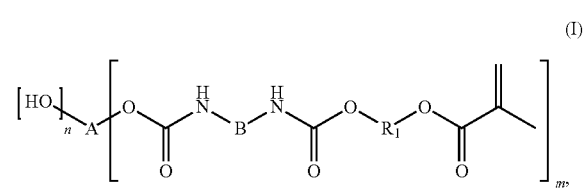

in which

B is an aromatic hydrocarbon group comprising two condensed benzene rings, wherein the benzene rings may optionally be substituted with alkyl groups, A is a linear or branched aliphatic $C_3$-$C_{10}$ alkylene group, each $R_1$, respectively independently of one another, is a branched or linear aliphatic $C_1$-$C_{15}$ alkylene group, n is a whole number greater than or equal to 0, and m is a whole number greater than or equal to 3.

2. The compound according to claim 1, wherein $R_1$ is a $C_2$ alkylene group or $C_3$-alkylene group.

3. The compound according to claim 1, wherein the linear or branched aliphatic $C_3$-$C_{10}$ alkylene group A is a trivalent or polyvalent group, as is obtained by removal of the hydroxyl groups from a trifunctional or polyfunctional alcohol.

4. The compound according to claim 1, wherein n=0, 1 or 2 and m=3, 4 or 5.

5. The compound according to claim 4, wherein n=0 or 1 and m=3, 4 or 5, with n+m=4 or 5.

6. A method for production of a reactive resin or of a reactive-resin component for construction purposes, the method comprising:
incorporating the compound according to claim 1 as a component of a reactive resin or of a reactive-resin component.

7. A method for increasing the bond strength of a cured fastening caulk, the method comprising:
mixing the compound according to claim 1 as a component of a fastening caulk, curing said fastening caulk, to obtain a fastening caulk having increased bond strength compared to a fastening caulk without the compound according to claim 1.

8. A reactive resin, comprising:
the compound according to claim 1,
an inhibitor,
an accelerator, and
optionally a reactive diluent.

9. A reactive-resin component, comprising:
the reactive resin according to claim 8.

10. A reactive-resin system, comprising:
the reactive-resin component (A) according to claim 9, and
a hardener component (B), which contains an initiator.

11. The reactive-resin system according to claim 10, wherein at least one of the components (A) or (B) contains an inorganic aggregate.

12. The compound according to claim 3, wherein the linear or branched aliphatic $C_3$-$C_{10}$ alkylene group A is a trivalent or tetravalent group, as is obtained by removal of the hydroxyl groups from a trifunctional or tetrafunctional alcohol.

13. A method of filling drilled holes for construction purposes, the method comprising:
mixing and applying a fastening caulk to said drilled hole, said fastening caulk comprising
the reactive resin according to claim 8, and
a hardener component.

14. A method of filling drilled holes for construction purposes, the method comprising:
mixing and applying the reactive-resin system according to claim 10 to said drilled hole.

15. A method for chemically fastening anchors in drilled holes, comprising:
mixing and applying a fastening caulk to said drilled hole, said fastening caulk comprising
the reactive resin according to claim 8, and
a hardener component.

16. A method for chemically fastening anchors in drilled holes, comprising:
mixing and applying the reactive-resin system according to claim 10 to said drilled hole.

* * * * *